(12) United States Patent
Saul et al.

(10) Patent No.: US 9,234,889 B1
(45) Date of Patent: Jan. 12, 2016

(54) METHOD AND TEST STRIP FOR DETECTING RESIDUES

(75) Inventors: Steven J. Saul, Arlington, MA (US); David W. Douglas, Kensington, NH (US)

(73) Assignee: Charm Sciences, Inc., Lawrence, MA (US)

(*) Notice: Subject to any disclaimer, the term of this patent is extended or adjusted under 35 U.S.C. 154(b) by 660 days.

(21) Appl. No.: 12/640,764

(22) Filed: Dec. 17, 2009

Related U.S. Application Data (60) Provisional application No. 61/138,761, filed on Dec. 18, 2008.

(51) Int. Cl.
G01N 33/537 (2006.01)
G01N 33/543 (2006.01)

(52) U.S. Cl.
CPC ........ *G01N 33/537* (2013.01); *G01N 33/54353* (2013.01)

(58) Field of Classification Search
USPC ......... 436/514, 518, 524–534, 536, 538–541, 436/20–23, 924; 435/7.1, 287.1–287.3, 435/287.7–287.9, 970
See application file for complete search history.

(56) References Cited

U.S. PATENT DOCUMENTS

| | | |
|---|---|---|
| 4,700,714 A | 10/1987 | Fuisz |
| 4,703,017 A | 10/1987 | Campbell et al. |
| 4,743,560 A | 5/1988 | Campbell et al. |
| 4,826,759 A | 5/1989 | Guire et al. |
| 4,999,285 A | 3/1991 | Stiso |
| 5,238,652 A | 8/1993 | Sun et al. |
| 5,260,222 A | 11/1993 | Patel et al. |
| 5,266,497 A | 11/1993 | Imai et al. |
| 5,296,347 A | 3/1994 | LaMotte, III |
| 5,434,053 A | 7/1995 | Piasio |
| 5,451,504 A | 9/1995 | Fitzpatrick et al. |
| 5,521,102 A | 5/1996 | Boehringer et al. |
| 5,545,721 A | 8/1996 | Carroll et al. |
| 5,602,040 A | 2/1997 | May et al. |
| 5,622,871 A | 4/1997 | May et al. |
| 5,656,448 A | 8/1997 | Kang et al. |
| 5,656,502 A | 8/1997 | MacKay et al. |
| 5,714,389 A | 2/1998 | Charlton et al. |
| 5,726,010 A | 3/1998 | Clark |
| 5,726,013 A | 3/1998 | Clark |

(Continued)

FOREIGN PATENT DOCUMENTS

| | | |
|---|---|---|
| EP | 0321145 A3 | 3/1990 |
| EP | 0291176 B1 | 11/1991 |

(Continued)

OTHER PUBLICATIONS

ThermoScientific, Choosing a seondary antibody: A guide to fragment specificity, 2007, pp. 1-4.*

(Continued)

*Primary Examiner* — Erik B Crawford
(74) *Attorney, Agent, or Firm* — Richard J. Long; Leslie Meyer-Leon (57) ABSTRACT

A method and test strip for detecting one or more analytes in a test solution. The method and test strip include a detectable component, such as a gold particle, that is linked to a binder, such as an antibody, through a linkage. The linkage can include an antibody binding protein and an antispecies antibody.

30 Claims, 1 Drawing Sheet

(56) References Cited

U.S. PATENT DOCUMENTS

| | | | |
|---|---|---|---|
| 5,739,041 | A | 4/1998 | Nazareth et al. |
| 5,753,517 | A | 5/1998 | Brooks et al. |
| 5,874,216 | A | 2/1999 | Mapes |
| 5,985,675 | A | 11/1999 | Charm et al. |
| 6,001,658 | A | 12/1999 | Fredrickson |
| D419,439 | S | 1/2000 | Markovsky et al. |
| 6,177,281 | B1 | 1/2001 | Manita |
| 6,319,466 | B1 | 11/2001 | Markovsky et al. |
| 6,475,805 | B1 | 11/2002 | Charm et al. |
| RE38,430 | E | 2/2004 | Rosenstein |
| 7,410,808 | B1 * | 8/2008 | Saul et al. ............ 436/518 |
| 7,763,433 | B2 * | 7/2010 | Danks et al. ............ 435/7.1 |
| 2008/0176342 | A1 * | 7/2008 | Granier ............ 436/530 |
| 2010/0279310 | A1 * | 11/2010 | Sia et al. ............ 435/7.1 |

FOREIGN PATENT DOCUMENTS

| | | | |
|---|---|---|---|
| EP | 0516095 | A2 | 2/1992 |
| EP | 0279574 | B1 | 8/1992 |
| EP | 0582231 | A1 | 2/1994 |
| EP | 0378391 | B1 | 9/1995 |
| EP | 0306336 | B2 | 12/1997 |
| EP | 0593112 | B1 | 8/1998 |
| EP | 0284232 | B2 | 10/2002 |
| EP | 0291194 | B2 | 7/2003 |
| EP | 0299428 | B2 | 1/2004 |
| WO | 90/15327 | A1 | 12/1990 |
| WO | 94/02850 | A1 | 2/1994 |
| WO | 94/23300 | A1 | 10/1994 |
| WO | 96/38720 | A1 | 12/1996 |
| WO | 97/03209 | A1 | 1/1997 |
| WO | 97/05287 | A1 | 2/1997 |
| WO | 02/010708 | A3 | 8/2003 |
| WO | WO 2006089027 | A2 * | 8/2006 |

OTHER PUBLICATIONS

Lipman et al., Monoclonal Versus Polyclonal Antibodies: Distinguishing Characteristics, Applications, and Information Resources, 2005, vol. 46, No. 3, pp. 258-268.*
Bangs Laboratories, Inc.; TechNote 100: Polymer Microspheres; Jan. 29, 2010; pp. 1-3; Rev.#001; http://www.bangslabs.com/files/bangs/docs/pdf/100.pdf.
Bangs Laboratories, Inc.; TechNote 101: ProActive Microspheres; Apr. 9, 2008; pp. 1-8; Rev.#007; http://www.bangslabs.com/files/bangs/docs/pdf/101.pdf.
Bangs Laboratories, Inc.; TechNote 102: Magnetic Microspheres; Aug. 25, 2010; pp. 1-5; Rev.#010; http://www.bangslabs.com/files/bangs/docs/pdf/102.pdf.
Bangs Laboratories, Inc.; TechNote 103: Fluorescent/Dyed Microspheres; May 6, 2010; pp. 1-7; Rev.#008; http://www.bangslabs.com/files/bangs/docs/pdf/103.pdf.
Bangs Laboratories, Inc.; TechNote 104: Silica Microspheres; Apr. 9, 2008; pp. 1-2; Rev.#003; http://www.bangslabs.com/files/bangs/docs/pdf/104.pdf.
Bangs Laboratories, Inc.; TechNote 105: Microsphere Size Standards; Sep. 7, 2007; pp. 1-2; Rev. #003; http://www.bangslabs.com/files/bangs/docs/pdf/105.pdf.
Bangs Laboratories, Inc.; TechNote 106: Confocal Standards; Aug. 13, 2007; pp. 1-4; Rev.#003; http://www.bangslabs.com/files/bangs/docs/pdf/106.pdf.
Bangs Laboratories, Inc.; TechNote 201: Working with Microspheres; Apr. 10, 2008; pp. 1-20; Rev.#003; http://www.bangslabs.com/files/bangs/docs/pdf/201.pdf.
Bangs Laboratories, Inc.; TechNote 201A: Microsphere Selection; Sep. 10, 2008; pp. 1-4; Rev.#001; http://www.bangslabs.com/files/bangs/docs/pdf/201A.pdf.
Bangs Laboratories, Inc.; TechNote 202: Microsphere Aggregation; Apr. 9, 2009; pp. 1-4; Rev.#003; http://www.bangslabs.com/files/bangs/docs/pdf/202.pdf.
Bangs Laboratories, Inc.; TechNote 203: Washing Microspheres; Apr. 9, 2008; pp. 1-5; Rev.#002; http://www.bangslabs.com/files/bangs/docs/pdf/203.pdf.
Bangs Laboratories, Inc.; TechNote 204: Absorption to Microspheres; Apr. 9, 2008; pp. 1-6; Rev.#002; http://www.bangslabs.com/files/bangs/docs/pdf/204.pdf.
Bangs Laboratories, Inc.; TechNote 205: Covalent Coupling; Apr. 10, 2008; pp. 1-11; Rev.#004; http://www.bangslabs.com/files/bangs/docs/pdf/205.pdf.
Bangs Laboratories, Inc.; TechNote 206: Equations; Aug. 10, 2009; pp. 1-3; Rev.#003; http://www.bangslabs.com/files/bangs/docs/pdf/206.pdf.
Bangs Laboratories, Inc.; TechNote 208: Microsphere Sizing; Aug. 10, 2009; pp. 1-2; Rev.#002; http://www.bangslabs.com/files/bangs/docs/pdf/208.pdf.
Bangs Laboratories, Inc.; TechNote 301: Immunological Applications; Apr. 11, 2008; pp. 1-17; Rev.#002; http://www.bangslabs.com/files/bangs/docs/pdf/301.pdf.
Bangs Laboratories, Inc.; TechNote 302: Molecular Biology; Apr. 10, 2008; pp. 1-6; Rev.#003; http://www.bangslabs.com/files/bangs/docs/pdf/302.pdf.
Bangs Laboratories, Inc.; TechNote 303: Lateral Flow Tests; Apr. 11, 2008; pp. 1-7; Rev.#002; http://www.bangslabs.com/files/bangs/docs/pdf/303.pdf.
Bangs Laboratories, Inc.; TechNote 304: Light-Scattering Assays; Apr. 11, 2008; pp. 1-9; Rev.#002; http://www.bangslabs.com/files/bangs/docs/pdf/304.pdf.
Brady et al.; Resistance Development Potential of Antibiotic/Antimicrobial Residue Levels Designated as "Safe Levels"; Journal of Food Protection; Mar. 1993, pp. 229-233; vol. 56, No. 3.
Charm; An Integrated System Monitoring Milk for FDA "Safe Levels" Using Charm Test Methods; Journal of the Association of Food and Drug Officials; Jan. 1994; pp. 17-29; vol. 58, No. 1.
Charm et al.; Microbial Receptor Assay for Rapid Detection and Identification of Seven Families of Antimicrobial Drugs in Milk: Collaborative Study; Journal of the Association of Official Analytical Chemists; 1998; pp. 304-316; vol. 71, No. 2.
Duffy et al.; Measuring Microsphere Binding Capacity; IVD Technology; 1998; pp. 28-34; vol. 4, No. 7.
Haasnoot et al.; Evaluation of a Sol Particle Immunoassay (SPIA) based Single-step Strip Test for the Detection of Sulfadimidine Residues; Euroresidue III Conference; May 1996; pp. 461-465; Veldhoven, Netherlands.
Hermanson; Bioconjugate Technigues; 1996; pp. 169-186; Academic Press, Inc.; San Diego, CA, USA.
Hermanson et al.; Immobilized Affinity Ligand Techniques; 1992; pp. 98-111; Academic Press, Inc.; San Diego, CA, USA.
Millipore; A Short Guide: Developing Immunochromatographic Test Strips; 1996; pp. 1-36; Lit No. TB500; Millipore Corporation, Bedford, MA, USA.
Verheijen et al.; Single-step Strip Tests for Residue Analyses; Jun. 3, 1998; p. 1; DLO-State Institute for Quality Control of Agricultural Products; Wageningen, Netherlands.
Wong; Chemistry of Protein Conjugation and Cross-Linking; 1991; pp. 39-40, 122-123, 195-204; CRC Press, Inc. Boca Raton, Florida, USA.

\* cited by examiner

METHOD AND TEST STRIP FOR DETECTING RESIDUES

REFERENCE TO PRIOR APPLICATIONS

The present application claims the benefit of and priority to U.S. Provisional Application Ser. No. 61/138,761, filed Dec. 18, 2008, the contents of which are incorporated herein by reference in its entirety.

BACKGROUND

Residues of antibiotics and other toxins in foods are a major food safety concern. Food is tested worldwide for antibiotics, mycotoxins and other contaminants. One type of test method uses what is commonly known as a lateral flow test strip.

Lateral-flow test strips for detecting one or more analytes in a fluid sample may include a capture agent immobilized within a region of the test sometimes referred to as a detection zone. Detection zones can include test zones and control zones. A typical capture agent has binding affinity for a substance that may be in a mobile phase of the test strip.

Lateral-flow tests in which the binding of a substance from a mobile phase to a capture agent generates a visible signal, that can be interpreted visually or using a reader, such as a spectrophotometer, are well known in the art. Examples of such tests are described in U.S. Pat. No. 5,985,675, issued Nov. 16, 1999; and U.S. Pat. No. 6,319,466, issued Nov. 20, 2001, and U.S. patent application Ser. No. 10/289,089, filed Nov. 6, 2002 (based on U.S. Provisional Application 60/332,877, filed Nov. 6, 2001), and U.S. Pat. No. 7,410,808, issued Aug. 12, 2008, all of which are incorporated herein by reference. Many such tests utilize a signal component, such as a colored particle, to generate the visible signal. Other such tests utilize a reaction, such as an enzyme-substrate reaction, to generate the visible signal. Generally, tests require a binding substance to be linked to the signal component. If the binding of the binding substance to the signal component is weak or inconsistent, an additional linkage may be necessary.

SUMMARY

Disclosed herein are methods and devices for linking a binding substance (binder) to a signal component of a test to form a detectable binder. One category of tests in which such a linkage can be useful includes a lateral flow test strip type test for detection of a contaminant in a sample. Detectable contaminants may include antigens, haptens and their antibodies, hormones, vitamins, drugs, metabolites and their receptors and binding materials, antibiotics, such as beta-lactams, cephalosporins, erythromycin, sulfonamides, tetracyclines, nitrofurans, quinolones, vancomycin, gentamicin, amikacin, chloramphenicol, streptomycin and tobramycin and toxins, such as mycotoxins, including aflatoxin, ochratoxin and vomitoxin.

Tests can include one or multiple binders each with binding affinity for one or more analytes. One or more test zones, and one or more control zones, including various capture agents with binding affinity for the binders, can be included.

An aspect includes a test for detection of ochratoxin. An ochratoxin binder, such as mouse anti-ochratoxin antibody, can be linked to a detectable component, such as a gold particle, for detection. In such a test, a test zone can contain a capture agent for the binder, such as an ochratoxin conjugate, ochratoxin or ochratoxin analogue. Immobilization of the ochratoxin can be through use of a carrier protein, such as BSA. Linking of the binder to the detectable component can be through a linkage described herein.

Another aspect includes a test for detection of beta-lactam antibiotics. Test strips can be sensitive to penicillin G, amoxicillin, ampicillin, ceftiofur, cephapirin and cloxacillin. Sensitivity is preferably at or below government determined acceptable levels ("safe levels"). Such a test can include a binder for beta-lactam antibiotics, for example a beta-lactam binding protein derived from *Geobacillus stearothermophilus* (sometimes referred to as *Bacillus stearothermophilus*) ("B.st.") with affinity to multiple beta-lactams including the target beta-lactams ("the BL binder"). Generally binders with affinity to multiple drugs are hereinafter referred to as "multianalyte binders". Such binders can be linked to a signal component, such as a gold particle, for detection.

A beta-lactam test can also include a binder with greater specificity for a particular analyte as compared to a multianalyte binder, hereinafter referred to as a "specific binder", for example an antibody to an antibiotic such as cloxacillin ("cloxacillin binder") to which the multianalyte binder, such as the BL binder, may not have sensitivity at or below the safe levels.

Depending on the affinity of a binder to a signal component, an additional linkage may be helpful. For example, ochratoxin antibody and/or cloxacillin antibody can be linked to gold particles through a linkage. In some aspects the linkage includes protein A bound to the gold particle and to an anti-species antibody. Other aspects include a direct anti-species linkage (without an antibody binding protein such as protein A) between a gold particle and ochratoxin antibody or cloxacillin antibody.

The test can also utilize two or more binders having sensitivity for unrelated analytes such as different families of antibiotics or toxins.

An optional control zone can be used for comparison to one or more test zones or as a signal that the test functioned properly and is complete. A control zone can also include a capture agent. In an example in which a linkage is used to link a binder, such as an antibody, to a signal component, the control zone can include, as a capture agent, an antibody to a component of the linkage. For example, when an anti-species antibody is used to link the binder to the signal component the control zone can include, as a capture agent, an antibody to the species that was the source of the anti-species antibody. For example, if the anti-species linkage includes a rabbit anti-mouse or rabbit anti-sheep antibody, then the control zone can include a goat anti-rabbit antibody.

DETAILED DESCRIPTION

Often a substance such as an agricultural product has one or more analytes to be detected. To detect an analyte a binder for the analyte can be employed. The binder can be a binding protein such as an enzyme, antibody, receptor or other substance capable of binding to the analyte to form an analyte-binder complex. The binder, or analyte-binder complex, can be detected through various methods including labeling the binder, and, therefore, the resulting complex, with a visible label (signal component), such as a gold particle, and capturing the labeled complex with a capture agent.

In embodiments utilizing a lateral flow test strip, the strip can include a solid support, such as nitrocellulose with sufficient pore size to allow liquid to flow along the membrane. A separate region can be included for applying a fluid sample ("sample pad"). The test strip can include one or a plurality of binders selected for their binding affinity to the analytes to be detected. Binders can be located on the sample pad or elsewhere on the test strip.

In an example of using the test strip, fluid is applied to a sample pad. The sample fluid solubilizes the binders and migrates through the test strip by the forces of lateral capillary flow. The binders bind to analyte in the sample. The fluid flows to a detection zone. The detection zone can include one or more test zones and one or more control zones, each containing capture agents.

In an example, a test zone capture agent can be, for example, an analyte, representative analyte, or analyte analogue. The capture agent at some point must be immobilized to the strip so that it is either removed from sample flow or is not solubilized by sample fluid flow. Immobilization on the strip, so that the capture agent is not solubilized by fluid flow, can be accomplished using a carrier protein such as bovine serum albumin (BSA), or other carrier protein well known in the art, for example ovalbumin (OVA) or keyhole limpet hemocyanin (KLH).

Each test zone capture agent captures all or a portion of the binder, which is not already bound with sample analyte, from what is known as the mobile phase. A binder that is bound by analyte from the sample tends not to be captured at the test zone. Binders that are not captured at the test zone can be captured in the control zone or flow through to a disposal pad.

In an embodiment, a specific binder is a cloxacillin binder and a multianalyte binder is a BL binder. Both the cloxacillin binder and the BL binder can be detectably labeled with a signal component, for example gold particles. The labeled cloxacillin binder and labeled beta-lactam binder can be combined in a solution and applied, for example, by spraying, within or proximate to a pretreated POREX® (POREX is a registered trademark of Porex Technologies Corp, Georgia USA) sample pad in contact with a nitrocellulose membrane. The binders can also be combined with the sample in a container, such as a test tube, and added to the test strip with the sample. When exposed to a sample such as fluid milk, the cloxacillin binder binds to cloxacillin in the milk and the BL binder binds to beta-lactams (including to some extent cloxacillin) in the milk to form complexes. Lateral capillary flow carries the complexes, and any uncomplexed labeled binders, to the test zone area of the strip.

In an embodiment using two binders, multiple test zones can be employed to capture the binders in separate zones. In an example in which cloxacillin binder and BL binder are used, the first test zone capture agent can include immobilized cloxacillin and the second test zone capture agent can include an immobilized different beta-lactam, such as ceforanide. In the test zones, the capture agents can capture the binders that have not been previously bound by sample analyte. Such attachment at the test zone can generate a visible signal when a signal component, such as gold or other label well known in the art, is used.

Labels other than gold include other particles including, but are not limited to, colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles, colloidal metal ferrite particles, any of the above-mentioned colloidal particles coated with an organic or inorganic layer; protein or peptide molecules; liposomes; or organic polymer latex particles, such as polystyrene latex beads. Other labels may also be useful including, but not limited to, luminescent labels; fluorescent labels; or chemical labels, such as electroactive agents (e.g., ferrocyanide); enzymes; radioactive labels; or radiofrequency labels.

In an embodiment in which gold particle is used it is necessary to link the binder, whether it is a receptor isolated from a bacteria, an antibody, antibody fragment, synthetic binder or another type of binder, to the gold particle. In an embodiment, a mouse antibody, such as an ochratoxin antibody, is linked to a gold particle via a linkage that includes an anti-species antibody such as a rabbit anti-mouse antibody or goat anti-mouse antibody. Some embodiments also include an antibody binding protein, such as protein A, in the linkage. Similar linkages can include other antibody binding proteins, for example protein G, protein A/G and protein L, and anti-mouse antibodies from species other than rabbits or goats. Similarly, if the binder is a non-mouse antibody, such as a sheep antibody, the linkage can include an anti-sheep antibody such as a rabbit anti-sheep antibody. Typically the linkage will include an anti-species antibody which is anti to the species source of the antibody and an antibody binding protein that binds to the anti-species antibody. The antibody binding protein being bound both to the, for example, gold particle and the anti-species antibody, such as rabbit anti-mouse, with the anti-species antibody bound to both the antibody binding protein, such as protein A, and the species antibody, such as mouse antibody. In such an embodiment, the linkage includes both the antibody binding protein and the anti-species antibody.

In embodiments utilizing a linkage that includes a rabbit anti-species antibody, such as a rabbit anti-sheep or rabbit anti-mouse antibody, a control zone can include an anti-rabbit antibody such as a goat anti-rabbit antibody.

In an embodiment, detectably labeled binders are combined with unlabeled binders, such as unlabeled antibodies. The unlabeled antibodies are selected for their affinity to antibiotics to which the other binders, for example a multianalyte binder, are overly sensitive. Such unlabeled binders can compete with labeled multianalyte binders for a specific antibiotic and, thereby, reduce test sensitivity to the antibiotic/analyte to which the unlabeled binders have affinity. The unlabeled binders can have affinity for some or all of the analyte to which the labeled multianalyte binder has affinity. By including unlabeled binders with affinity for some, but not all, of the analytes to which a competing labeled binder has affinity, sensitivity of the test to those selected antibiotics/analytes will be reduced.

In certain embodiments, in a negative sample the control zone will capture fewer labels (signal components) as compared to any one of the one or more test zones. In a positive sample for a single analyte or family, the control zone will capture more labels than any one of the test zones.

Including multiple capture agents at the control zone provides the possibility of a test strip for detection of multiple analytes such as multiple antibiotics. For example, a test strip to detect sulfonamides, tetracyclines, amphenicols or macrolides, possibly combined on a test strip to detect beta-lactams, with a single control zone for comparison to multiple test zones for the different antibiotics. A control zone can have specific antibodies to particular binders, multianalyte binder antibodies, antibody binding proteins or combinations thereof. Similarly, the control zone can include multiple antibodies of different host species and not necessarily include a general antibody binder. For example, if one binder is a mouse monoclonal antibody and another is a rabbit polyclonal antibody, the control zone can include an anti-mouse antibody and an anti-rabbit antibody. In an example in which a linkage is used to link a binder, such as an antibody, to a signal component, the control zone can include an antibody to a component of the linkage. For example, when an anti-species antibody is used to link the binder to the signal component the control zone can include an antibody to the species that was the source of the anti-species antibody. For example, if the anti-species linkage includes a rabbit anti-mouse or rabbit anti-sheep antibody, then the control zone can include a goat anti-rabbit antibody.

In another embodiment, the assay can be in the form of a so-called sandwich assay. In such an embodiment, as with the other embodiments described herein in which the non-sandwich format is used, either the analyte binder can be labeled with a visible label such as a gold particle and use a linkage to the label including an antibody binding protein and a anti-species antibody providing the linkage between the label and the analyte binder.

DESCRIPTION OF THE DRAWINGS

Figure 1:
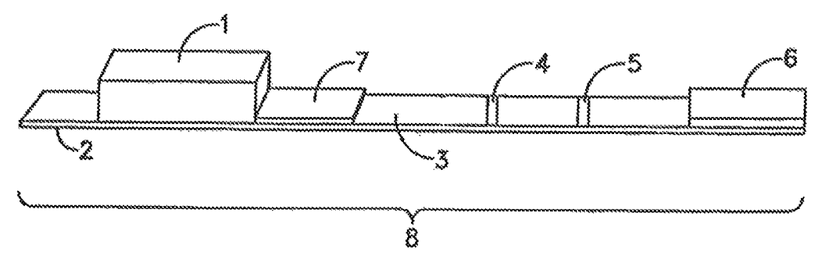
FIG. 1 is a perspective view of the test strip embodiment.

FIG. 1 shows the test strip apparatus 8, comprised of nitrocellulose membrane 3 and POREX® 7 attached to solid support 2. Sample is contacted to sample pad-sponge 1. Sample flows from sample pad 1 to POREX 7 containing mobile phase binder linked to the detectable component, for example through a linkage comprising antispecies antibody and antibody binding protein. Binder will bind analyte from the sample and flow along the nitrocellulose membrane 3 to test line 4. A portion of binder unbound by sample analyte will bind to the test line. Remaining unbound binder and analyte-binder complex will flow to control line 5. A portion of said unbound binder and a portion of analyte-binder complex, will bind at the control line. The control line is compared to the test line to determine a result.

EXAMPLES

Example 1

Lateral Flow Test to Detect Ochratoxin

Mouse Anti-Ochratoxin Antibody was Linked to a Gold Particle by a Linkage as Follows:

To prepare the anti-ochratoxin bead a 375 milliliters (ml) batch of gold beads were combined with 500 micrograms (μg) of protein A diluted in 5 millimolar (mM) diethanolamine buffer at pH 8.0 and mixed for 10 minutes. 20 ml of blocking buffer, containing 20% Peg 20,000, 0.12% chaps in 10 mM Popso at pH 7.25 and 0.04% PROCLIN 300 (PROCLIN is a registered trademark of ROHM AND HAAS COMPANY Philadelphia Pa.) was added. After at least 1 hour 500 μg of rabbit anti-mouse antibody was added. The mixture was reacted overnight with stirring. Next, 175 μg of anti-ochratoxin mouse monoclonal was added and allowed to react for ten minutes with stirring. The bead solution was then centrifuged at 9000 revolutions per minute (rpm) in a Sorvall SLA-3000 rotor for 50 minutes. The supernatant was discarded and the bead pellet dissolved in 6 ml of water. The dissolved pellet was filtered through a 0.45 micrometers (μm) cellulose acetate filter. The peak absorbance of the beads was targeted between 525 and 540 nanometers (nm). The solution was diluted with water to a volume that would give an absorbance of 0.167 when 10 microliters (μl) is added to 3 ml of water. Glycerol was added to a final concentration of approximately 16.7%. The beads were diluted to a concentration of 20 to 30% with 40% sucrose for spraying onto the POREX. A Bio-dot sprayer is used to spray four lines of beads onto POREX at a rate of 0.8 microliters per centimeter (μl/cm). The POREX was previously treated with a buffer solution containing 2% gelatin, 2% sucrose, 0.01% chaps and 0.04% PROCLIN 300 in 10 mM pipes buffer at pH 7.3 and dried.

The Test Zone (Line) was Prepared as Follows:

The test zone includes ochratoxin-BSA. The conjugate was prepared by converting ochratoxin to an amino derivative by adding 1-Ethyl-3-[3-dimethylaminopropyl]carboiimide (EDC) and N-hydroxysuccinimide (NHS) to the ochratoxin in a buffer containing a diamine. 25 milligrams (mg) of ochratoxin was dissolved in 2 ml of dimethyl sulfoxide (DMSO) and 13 ml of 0.05 M 4-morpholineethanesulfonic acid (MES) at pH 7.4 containing 0.2 molar (M) diaminopropane. EDC (500 mg) and 100 mg of NHS were then added to the reaction, mixed and the reaction incubated at 45° C. The reaction was run on high pressure liquid chromatography (HPLC) to monitor the conversion to the ochratoxin amine derivative. After the reaction was complete the buffer was removed by binding the ochratoxin amine to an activated C18 solid phase extraction column. The column was further washed with approximately 50 ml of water and the ochratoxin amine derivative was eluted with methanol and dried under a stream of nitrogen. The derivative was then dissolved in DMSO and converted to a sulfhydryl derivative with Traut's reagent and reacted with Sulfo-SMCC activated BSA. 184 mg of sulfhydryl blocked BSA was dissolved in 0.16 M borate buffer at pH 8.0 containing 5 mM EDTA and mixed with 22 mg of Sulfo-SMCC dissolved in 1 ml of DMSO. The reaction was mixed for approximately 2 hours at room temperature and then desalted against 0.02 M sodium phosphate buffer at pH 6.9. One hour and fifteen minutes into this reaction the ochratoxin derivative was dissolved in 6 ml of DMSO and added to 6 ml of a 0.16 M sodium borate at pH 8.0 containing 5 mM EDTA to which 7.5 mg of Traut's reagent was added and reacted for approximately 30 minutes. The solution was brought to a pH between 6.5 and 7.0 with 0.4 M sodium phosphate buffer. The two reactions were mixed and the reaction mixed overnight at room temperature. The reaction was then desalted against 0.02 M phosphate buffer, pH 7.2, precipitated with ammonium sulfate, centrifuged, and the pellet dissolved in 0.02 M phosphate buffer, pH 7.2 and then desalted again in a desalting column and equilibrated with 0.02 M phosphate buffer, pH 7.2.

The oxchratoxin BSA derivative was diluted 40 fold in 0.01 M phosphate buffer pH 6.9 containing 25% sucrose and sprayed onto nitrocellulose 0.8 μl/cm using equipment from Biodot sprayed 13 mm from the edge with the drying towers set to 75° C.

The Control Zone (Line) was Prepared as Follows:

The control zone included an affinity purified in-house goat anti-rabbit antibody that was diluted 25 fold in 0.01 M phosphate buffer at pH 7.2 containing 5% sucrose. The mixture was sprayed at the same time as the conjugate at a flow rate of 1.0 microliter (μl)/centimeter (cm) at a position 17 mm from the edge.

The following results, presented in Tables 1-34, were from experiments utilizing ochratoxin detection tests prepared as described above. Matrices included wine (tables 1-5), barley (tables 6-14) and wheat (tables 15-34).

Each result is the average of 10 test results. A ROSA READER (ROSA is a registered trademark of Charm Sciences, Inc. Lawrence, Mass.) was used to read test results from the test strips. Results under the heading T are reflectance results from the test zone. Results under the heading C are reflectance results from the control zone. "Result" data is the actual difference between the control zone (C) and the test zone (T). Percent coefficient of variation (% CV) is determined by comparing the 10 results the average of which 10 results is provided in the tables. Table headings include parts per billion (ppb) concentrations of ochratoxin in the particle samples tested.

TABLE 1

| 0 ppb | | | |
|---|---|---|---|
| | T | C | Result |
| Result | 4167 | 2475 | −1692 |
| % CV | 8% | 8% | 13% |

TABLE 2

| 0.5 ppb | | | |
|---|---|---|---|
| | T | C | Result |
| Result | 3766 | 2743 | −1023 |
| % CV | 5% | 3% | 15% |

TABLE 3

| 1 ppb | | | |
|---|---|---|---|
| | T | C | Result |
| Result | 3218 | 2843 | −376 |
| % CV | 15% | 6% | 91% |

TABLE 4

| 2 ppb | | | |
|---|---|---|---|
| | T | C | Result |
| Result | 2511 | 3260 | 748 |
| % CV | 7% | 6% | 28% |

TABLE 5

| 5 ppb | | | |
|---|---|---|---|
| | T | C | Result |
| Result | 1089 | 3538 | 2450 |
| % CV | 13% | 3% | 8% |

TABLE 6

| 0 ppb | | | |
|---|---|---|---|
| | T | C | Result |
| Result | 4228 | 2213 | −2015 |
| % CV | 3% | 7% | 6% |

TABLE 7

| 0.625 ppb | | | |
|---|---|---|---|
| | T | C | Result |
| Result | 4094 | 2330 | −1764 |
| % CV | 2% | 6% | 5% |

TABLE 8

| 1.25 ppb | | | |
|---|---|---|---|
| | T | C | Result |
| Result | 3899 | 2506 | −1393 |
| % CV | 5% | 6% | 8% |

TABLE 9

| 2.5 ppb | | | |
|---|---|---|---|
| | T | C | Result |
| Result | 3370 | 2582 | −788 |
| % CV | 9% | 4% | 29% |

TABLE 10

| 5 ppb | | | |
|---|---|---|---|
| | T | C | Result |
| Result | 2601 | 3095 | 494 |
| % CV | 11% | 9% | 13% |

TABLE 11

| 10 ppb | | | |
|---|---|---|---|
| | T | C | Result |
| Result | 1186 | 3747 | 2561 |
| % CV | 14% | 2% | 7% |

TABLE 12

| 10 ppb | | | |
|---|---|---|---|
| | T | C | Result |
| Result | 3427 | 3032 | −395 |
| % CV | 6% | 4% | 45% |

TABLE 13

| 20 ppb | | | |
|---|---|---|---|
| | T | C | Result |
| Result | 2452 | 3397 | 945 |
| % CV | 5% | 5% | 19% |

TABLE 14

| 100 ppb | | | |
|---|---|---|---|
| | T | C | Result |
| Result | 416 | 4080 | 3664 |
| % CV | 26% | 6% | 7% |

TABLE 15

| | 0 ppb | | |
|---|---|---|---|
| | T | C | Result |
| Result | 4275 | 2135 | −2141 |
| % CV | 3% | 9% | 10% |

TABLE 16

| | 0.5 ppb | | |
|---|---|---|---|
| | T | C | Result |
| Result | 4022 | 2196 | −1827 |
| % CV | 3% | 5% | 9% |

TABLE 17

| | 1.25 ppb | | |
|---|---|---|---|
| | T | C | Result |
| Result | 3799 | 2450 | −1349 |
| % CV | 3% | 6% | 12% |

TABLE 18

| | 0.625 ppb | | |
|---|---|---|---|
| | T | C | Result |
| Result | 4077 | 2391 | −1686 |
| % CV | 4% | 6% | 12% |

TABLE 19

| | 2.5 ppb | | |
|---|---|---|---|
| | T | C | Result |
| Result | 3208 | 2695 | −513 |
| % CV | 10% | 7% | 48% |

TABLE 20

| | 5 ppb | | |
|---|---|---|---|
| | T | C | Result |
| Result | 2445 | 3183 | 737 |
| % CV | 10% | 5% | 22% |

TABLE 21

| | 10 ppb | | |
|---|---|---|---|
| | T | C | Result |
| Result | 1153 | 3465 | 2313 |
| % CV | 9% | 4% | 7% |

TABLE 22

| | 15 ppb | | |
|---|---|---|---|
| | T | C | Result |
| Result | 767 | 3537 | 2769 |
| % CV | 16% | 6% | 6% |

TABLE 23

| | 20 ppb | | |
|---|---|---|---|
| | T | C | Result |
| Result | 592 | 3681 | 3089 |
| % CV | 18% | 6% | 6% |

TABLE 24

| | 10 ppb | | |
|---|---|---|---|
| | T | C | Result |
| Result | 3704 | 3079 | −625 |
| % CV | 4% | 6% | 28% |

TABLE 25

| | 20 ppb | | |
|---|---|---|---|
| | T | C | Result |
| Result | 2591 | 3500 | 909 |
| % CV | 8% | 5% | 11% |

TABLE 26

| | 100 ppb | | |
|---|---|---|---|
| | T | C | Result |
| Result | 338 | 3956 | 3618 |
| % CV | 34% | 6% | 7% |

TABLE 27

| | x ppb | | |
|---|---|---|---|
| | T | C | Result |
| Result | 2684 | 3502 | 818 |
| % CV | 18% | 6% | 62% |

TABLE 28

| | 0 ppb | | |
|---|---|---|---|
| | T | C | Result |
| Result | 4056 | 2002 | −2054 |
| % CV | 6% | 6% | 10% |

TABLE 29

| 3.5 ppb | | | |
|---|---|---|---|
| | T | C | Result |
| Result | 2880 | 2994 | 114 |
| % CV | 9% | 3% | 174% |

TABLE 30

| 3.5 ppb | | | |
|---|---|---|---|
| | T | C | Result |
| Result | 3182 | 2956 | −226 |
| % CV | 12% | 4% | 122% |

TABLE 31

| 7 ppb | | | |
|---|---|---|---|
| | T | C | Result |
| Result | 1373 | 3139 | 1766 |
| % CV | 10% | 9% | 18% |

TABLE 32

| 7 ppb | | | |
|---|---|---|---|
| | T | C | Result |
| Result | 1462 | 3381 | 1919 |
| % CV | 18% | 6% | 6% |

TABLE 33

| 7 ppb | | | |
|---|---|---|---|
| | T | C | Result |
| Result | 1782 | 3168 | 1387 |
| % CV | 4% | 3% | 7% |

TABLE 34

| 10 ppb | | | |
|---|---|---|---|
| | T | C | Result |
| Result | 1101 | 3496 | 2395 |
| % CV | 9% | 1% | 5% |

Example 2

Lateral Flow Tests to Detect the Beta-Lactams Penicillin-G, Amoxicillin, Ampicillin, Cloxacillin, Ceftiofur and Cephapirin at Safe Level The first test zone solution includes a cloxacillin-BSA conjugate at 0.1-2 mg/ml, buffered with 10 millimolar (mM) sodium phosphate, pH 5.5-7.0, containing 20% sucrose. The mixture was sprayed 1.6 cm above the bottom edge of a nitrocellulose membrane at a rate of 0.6 µl/cm. The second test zone solution includes a ceforanide-BSA conjugate at 0.55-0.8 mg/ml in 10 mM sodium phosphate, pH 6.9, containing 15% sucrose sprayed onto nitrocellulose using a Biodot sprayer. The second test zone was sprayed 2.2 cm above the bottom edge of the nitrocellulose at a rate of 0.8 µl/L.

The ceforanide-BSA conjugate, was made by using the amino group on the ceforanide to add a sulfhydryl group. Next a cross-linking agent, for example, Sulfosuccinimidyl-4-(N-maleimidomethyl)cyclohexane-1-carboxylate (sulfo-SMCC), was added to link the sulfhydryl group on the ceforanide derivative to the amino group on the carrier protein.

The cloxacillin-BSA conjugate was made by activating the carboxyl group of cloxacillin with a carbodiimide and N-hydroxysulfosuccinimide (S—NHS) and subsequently binding the cloxacillin activated compound to amino groups on BSA. Cloxacillin (1 g) is dissolved in dry DMSO. The S—NHS was dissolved in dry DMSO and added to the cloxacillin solution. To this solution (approximately 30 ml), 0.5 ml of diisolpropyl carbodiimide was immediately added and the reaction allowed to proceed for 2 to 3 hours. The reaction was then extracted 3 times with dry petroleum ether and the DMSO portion was retained. The activated cloxacillin in DMSO was gradually added to a solution of BSA (4-g/70 ml) in 0.02 M sodium phosphate buffer at pH 7.2. This reaction was allowed to proceed overnight with mixing. The resulting cloxacillin-BSA conjugate was desalted to remove free cloxacillin.

In an alternative method for making the cloxacillin-BSA conjugate, dissolve 1 gram of sulfhydryl blocked BSA in 9 ml of 0.1 M potassium carbonate buffer at pH 10.0. While stirring add dropwise a cloxacillin solution (100 mg/ml in DMSO) to the BSA solution. Place in a 15 ml centrifuge tube and mix overnight in an orbital shaker. Neutralize the solution by adding 4.0 ml of 0.4 M phosphate buffer, pH 6.3. Desalt the reaction on FPLC using one high prep 26/10 desalting column equilibrated with 0.02 M phosphate buffer, pH 7.2. To give a theoretical substitution of moles of cloxacillin per mole of BSA of 5.0, 32.5 mg of cloxacillin or 0.325 ml is added to the BSA solution.

In this embodiment the gold label includes a combination of BL binder gold conjugate and monoclonal cloxacillin antibody (cloxacillin binder) gold conjugate including linkage of protein A and rabbit anti-mouse antibody. Approximately 30% of the solution includes gold coated with 600 units (U) of beta-lactam binder (one unit is defined as the amount of purified antibiotic binder able to bind 1000 counts per minute of radiolabeled antibiotic, such as when using the Charm II System) purified from B.st. and approximately 20% consists of gold coated, through a protein A-rabbit anti-mouse linkage, with 1000 U of purified cloxacillin binder.

The prepare the anti-cloxacillin bead a 375 ml batch of gold beads were combined with 500 µg of protein A diluted in 5 mM diethanolamine buffer at pH 8.0 and mixed for 10 minutes. 20 ml of blocking buffer, containing BSA 10%, 20 mM Sodium Phosphate at pH 7.20 and 0.04% PROCLIN 300, was added. After at least 1 hour 500 µg of rabbit anti-mouse antibody was added. The mixture was reacted for 10 minutes with stirring. Next, 1000-2500 U of anti-cloxacillin mouse monoclonal were added and the mixture was allowed to react for ten minutes with stirring. The bead solution was centrifuged at 9000 rpm in a SORVALL SLA-3000 (SORVALL is a registered trademark of THERMO FISHER SCIENTIFIC WALTHAM MASSACHUSETTS) rotor for 50 minutes. The supernatant was discarded and the bead pellet dissolved in 6 ml of water. The dissolved pellet was filtered through a 0.45 µm cellulose acetate filter. The peak absorbance of the beads was targeted between 525 and 540 nm. The solution was diluted with water to a volume that would give an absorbance of 0.167 when 10 µl is added to 3 ml of water. Glycerol was added to a final concentration of approximately 16.7%. The beads were diluted to a concentration of 20 to 30% with 40% sucrose and 10% BSA for spraying onto the POREX. A Bio-dot sprayer is used to spray four lines of beads onto POREX at a rate of 0.7 to 0.9 μl/cm with 2 to 4 passes onto POREX. The POREX was previously treated with a buffer solution containing 0.002 M Borate, 1% sucrose, and 0.05 mg/ml glutathione, pH 7.4 and dried.

The monoclonal antibody to cloxacillin was purified by ammonium sulfate precipitation at 50% saturation and dialyzed against 20 mM sodium phosphate buffer, pH 7.2, containing 50 mM sodium chloride and then purified using a protein A column.

The BL binder was purified by passing a solubilized receptor solution through a column containing a bound beta-lactam ligand possessing beta-lactam binding activity. As the impure receptor solution was passed through the column, the receptor was bound to the beta-lactam and retained on the column. The column was washed to further remove impurities and then an elution solution was used, containing hydroxylamine, to break the bond between the receptor and the beta-lactam allowing the receptor to be eluted from the column.

Control Zone

Preparation of Rabbit Anti-Receptor Antibody.

The antibody was made in rabbits using purified beta-lactam receptor from *Geobacillus stearothermophilus* as the immunogen. The rabbit anti-receptor antibody was purified on a protein A column and diluted to 5 mg/ml protein for storage. Rabbit anti-receptor was then diluted 150 times in 10 mM phosphate buffer, pH 6.95, containing 25% sucrose. The two dilute solutions were then combined and immobilized onto the nitrocellulose on the control zone by spraying the solution onto the control zone.

The invention claimed is:

1. A lateral flow test strip for detecting an analyte in a test solution, the test strip comprising:
    (a) a detectable component, the detectable component linked to a binder through a linkage to form a detectable binder, the detectable binder configured for generating a detectable signal, the linkage comprising: (i) an antibody binding protein; and (ii) an anti-species antibody, the anti-species antibody having affinity to the binder, and the antibody binding protein having affinity to both the detectable component and the anti-species antibody, and wherein the detectable binder is further configured to combine with the analyte from the solution to, through affinity of the binder, form a detectable binder-analyte complex;
    (b) a test zone on the test strip, the test zone comprising a first capture agent immobilized thereon, whereby said first capture agent captures the detectable binder when the detectable binder has not formed the detectable binder-analyte complex;
    (c) a control zone on the test strip, the control zone comprising a second capture agent immobilized thereon, wherein the second capture agent comprises an antibody to the anti-species antibody, and whereby said second capture agent can capture the detectable binder whether or not the detectable binder formed the detectable binder-analyte complex; and
    wherein the test strip is configured to allow the test solution and the detectable binder to flow first to the test zone and second to the control zone, and wherein capturing of the detectable binder at either the test zone or control zone generates a detectable signal and whereby a greater signal in the control zone, as compared to the test zone, indicates a positive result.

2. The lateral flow test strip of claim 1 wherein the antibody binding protein comprises protein A.

3. The lateral flow test strip of claim 1, wherein the analyte binder comprises an antibody.

4. The lateral flow test strip of claim 1 wherein the analyte comprises ochratoxin and wherein the analyte binder comprises an antibody to ochratoxin.

5. The lateral flow test strip of claim 1 wherein the first capture agent comprises a representative analyte.

6. The lateral flow test strip of claim 1, wherein the first capture agent is immobilized on a solid support through a carrier protein.

7. The lateral flow test strip of claim 6 wherein the carrier protein comprises bovine serum albumin.

8. The lateral flow test strip of claim 1, wherein the analyte comprises cloxacillin and wherein the analyte binder comprises an antibody to cloxacillin.

9. The lateral flow test strip of claim 1 wherein the analyte binder comprises a monoclonal antibody.

10. The lateral flow test strip of claim 1, wherein the analyte binder comprises a polyclonal antibody.

11. The lateral flow test strip of claim 1 wherein the anti-species antibody comprises a polyclonal antibody.

12. The lateral flow test strip of claim 1 wherein the anti-species antibody comprises a rabbit antibody.

13. The lateral flow test strip of claim 1 wherein the anti-species antibody comprises a rabbit anti-mouse antibody.

14. The lateral flow test strip of claim 1 wherein the anti-species antibody comprises a rabbit anti-sheep antibody.

15. The lateral flow test strip of claim 1 wherein the second capture agent comprises a goat anti-rabbit antibody.

16. The lateral flow test strip of claim 1 wherein the detectable component comprises colloidal gold.

17. The lateral flow test strip of claim 1, wherein said test strip is configured such that, on application, the test solution solubilizes the detectable binder and migrates through the lateral flow test strip by the forces of lateral capillary flow.

18. A lateral-flow test method for detecting one or more analytes in a test sample, the method comprising:
    (a) adding the test sample to the lateral flow test strip of claim 1;
    (b) allowing the sample to contact the detectable binder, so that the detectable binder reacts with the analyte to form the detectable binder-analyte complex;
    (c) allowing the detectable binder to come in contact with the first capture agent, wherein the detectable binder will react with the first capture agent generating the detectable signal, and wherein the test is negative for the detection of the one or more analytes when the signal from the test zone is greater than the signal in the control zone and the test is positive for the one or more analytes when the signal from the control zone is greater than the signal from the test zone.

19. The method of claim 18 wherein the antibody binding protein comprises Protein A.

20. The method of claim 18, wherein the binder comprises an antibody.

21. The method of claim 20 wherein the analyte comprises ochratoxin and wherein the antibody comprises an antibody to ochratoxin.

22. The lateral flow test strip of claim 18, wherein the detectable binder is applied to the test solution prior to being applied to the test strip.

23. The lateral flow test strip of claim 18, wherein the analyte comprises cloxacillin and wherein the analyte binder comprises an antibody to cloxacillin.

24. The lateral flow test strip of claim 18, wherein the analyte binder comprises a monoclonal antibody.

25. The lateral flow test strip of claim 18, wherein the analyte binder comprises a polyclonal antibody.

26. The lateral flow test strip of claim 18, wherein the anti-species antibody comprises a polyclonal antibody.

27. The lateral flow test strip of claim 18, wherein the anti-species antibody comprises a rabbit antibody.

28. The lateral flow test strip of claim 18, wherein the anti-species antibody comprises a rabbit anti-mouse antibody.

29. The lateral flow test strip of claim 18, wherein the anti-species antibody comprises a rabbit anti-sheep antibody.

30. A lateral flow test strip for detecting an analyte in a test solution, the test strip comprising:
  (a) a detectable component, the detectable component linked to a binder through a linkage to form a detectable binder, the detectable binder configured for generating a detectable signal, the linkage comprising: (i) an antibody binding protein; and (ii) an anti-species antibody, the anti-species antibody having affinity to the binder, and the antibody binding protein having affinity to both the detectable component and the anti-species antibody, and wherein the detectable binder is further configured to combine with the analyte from the solution to, through affinity of the binder, form a detectable binder-analyte complex;
  (b) a test zone on the test strip, the test zone comprising a first capture agent immobilized thereon, whereby said first capture agent captures the detectable binder when the detectable binder has not formed the detectable binder-analyte complex;
  (c) a control zone on the test strip, the control zone comprising a second capture agent immobilized thereon, wherein the second capture agent comprises an anti-rabbit antibody with affinity to the anti-species antibody, and whereby said second capture agent can capture the detectable binder whether or not the detectable binder formed the detectable binder-analyte complex; and
wherein the test strip is configured to allow the test solution and the detectable binder to flow first to the test zone and second to the control zone, and wherein capturing of the detectable binder at either the test zone or control zone generates a detectable signal and whereby a greater signal in the control zone, as compared to the test zone, indicates a positive result.

* * * * *